(12) United States Patent
Starwynn

(10) Patent No.: US 7,198,633 B1
(45) Date of Patent: Apr. 3, 2007

(54) LIGHT/ELECTRIC PROBE SYSTEM AND METHOD

(76) Inventor: Darren Starwynn, 3810 E. Desert Cove Ave., Phoenix, AZ (US) 85028

( * ) Notice: Subject to any disclaimer, the term of this patent is extended or adjusted under 35 U.S.C. 154(b) by 323 days.

(21) Appl. No.: 10/841,344

(22) Filed: May 7, 2004

Related U.S. Application Data

(60) Provisional application No. 60/487,394, filed on Jul. 15, 2003.

(51) Int. Cl.
*A61N 5/01* (2006.01)
*A61N 5/06* (2006.01)

(52) U.S. Cl. .................. 607/90; 128/898; 607/88

(58) Field of Classification Search ............ 250/200, 250/228; 607/88–94; 128/898
See application file for complete search history.

(56) References Cited

U.S. PATENT DOCUMENTS

| | | | | |
|---|---|---|---|---|
| 4,989,605 A | | 2/1991 | Rossen | |
| 5,304,207 A | * | 4/1994 | Stromer | ............ 607/3 |
| 5,409,482 A | * | 4/1995 | Diamantopoulos | ........... 606/13 |
| 5,464,436 A | * | 11/1995 | Smith | ............ 607/89 |
| 5,843,074 A | | 12/1998 | Cocilovo | |
| 6,608,293 B2 | * | 8/2003 | Kuderer | ........ 250/200 |
| 6,872,221 B2 | * | 3/2005 | Lytle | ............ 607/89 |
| 6,969,843 B1 | * | 11/2005 | Beach et al. | ......... 250/228 |
| 2002/0002391 A1 | * | 1/2002 | Gerdes | .......... 607/89 |
| 2002/0026225 A1 | * | 2/2002 | Segal | ............ 607/89 |
| 2002/0123781 A1 | * | 9/2002 | Shanks et al. | ............ 607/89 |
| 2002/0143373 A1 | * | 10/2002 | Courtnage et al. | ........... 607/91 |
| 2003/0130709 A1 | * | 7/2003 | D.C. et al. | ............ 607/88 |

* cited by examiner

*Primary Examiner*—Henry M Johnson, III
(74) *Attorney, Agent, or Firm*—Parsons & Goltry; Michael W. Goltry; Robert A. Parsons

(57) ABSTRACT

A stimulation probe system includes a light integrating chamber with a reflecting inner surface. A plurality of LEDs is mounted to introduce emitted light into the light integrating chamber. Each LED produces a different wavelength of light with the plurality of LEDs producing a range of light wavelengths. A hand-held probe includes a circular opening in communication with the chamber positioned to supply light from the chamber to the surface of a body. Electrical circuitry is programmable to activate one or more of the LEDs to produce substantially any light wavelength in the range of light.

20 Claims, 4 Drawing Sheets

LIGHT/ELECTRIC PROBE SYSTEM AND METHOD

CROSS-REFERENCE TO RELATED APPLICATIONS

This application claims the benefit of U.S. Provisional Application No. 60/487,394, filed 15 Jul. 2003.

FIELD OF THE INVENTION

This invention relates to a probe system and methods for application of electrical and/or light stimulation to human or animal bodies to cause or support beneficial effects on health and beauty.

BACKGROUND OF THE INVENTION

There are many forms of energy stimulation that, when applied to the human or animal body are commonly considered to cause or support beneficial effects on health and beauty. These forms of energy include electricity, magnetism, white or colored light, sound waves, heat, pressure and so-called subtle energy stimulation. It is believed by modern science that the basis for all of this is that the body's own external systems are energy-based, and sensitively respond to external energies through the principle of resonance. A wealth of research has shown that the body internally utilizes electricity and light to power and regulate most of its life functions. Research shows that electrical currents primarily work on the physiological level through nerve conduction, heartbeat, brain waves, healing processes and much more, while light primarily works in the body's communication network within itself and with the outer environment.

The body is attuned to respond to multiple forms of energy from the environment. For example, during a thunderstorm we see lightning, hear thunder, and sense the heightened electrical energy of the atmosphere. In communication with other people, we see and hear them and perhaps feel (sense) them. Research has shown that there are also many subtle energy interchanges between people that affect recordable electrical levels of the body's bio-energy.

Some of the most commonly used forms of energy stimulation used for medical purposes are electrical stimulation for pain control and healing acceleration, ultrasound sound wave stimulation for soft tissue physical therapies, and light stimulation for skin diseases, seasonal affective disorder (S.A.D.) and many other physical and emotional conditions. Electrical and light stimulation is also widely used in cosmetic work, such as facial toning and cellulite reduction. In most cases each form of stimulation is applied separately.

Energy stimulation works on the body through the principle of resonance. Resonance is defined as follows:

1. in physics, . . . response of an object or a system that vibrates in step or phase with an externally applied oscillatory force, or 2. the enhancement of an atomic, nuclear, or particle reaction . . . by excitation of internal motion in the system.

All the energy forms mentioned above are delivered as a specific frequency or wavelength. That frequency can create a positive or negative resonance with the part of the body being stimulated. Positive resonance tends to reinforce or enhance healthy physiological activity. Negative resonance tends to reduce, block or cancel out, such activity. Negative resonance could be helpful to suppress pain or inflammation in some acute disorders, but in beauty and health maintenance positive resonance is generally more useful. Most of the energy stimulation devices sold to the healthcare and cosmetic markets offer a very limited range of available outputs, with little or no ability to create precise resonance with the body. As a result, the likelihood of accurately creating positive resonance is diminished, and effectiveness is hit or miss.

The ancient art of acupuncture is based on applying specific forms of energy stimulation to specific points on the surface of the body, called acu-points. Energy is applied to the acu-points through the mechanical and electrical charges of metal needles, manual pressure, heat, sound, or light. There is a large difference in effect between applying energy to a broad region of the body and applying it to specific acu-points. General stimulation of regions can be valuable for some systemic effects, but specific point stimulation is considered more valuable for targeted health and beauty effects.

There are presently several ways to generate color light emissions. The simplest is to pass white light generated from incandescent, fluorescent, or LED sources, or from the sun, through filters that remove specified wavelengths, thus allowing a discrete color to be passed through. A blue filter, for example, will remove all visible colors except blue.

Light emitting diodes, or LEDs, are silicon microchips that emit light when electrically stimulated. By adding various chemical substances to the silicon, different colors can be generated. Lasers, another form of semiconductor diode, produce coherent light beams, and are available in a range of colors.

A type of LED called RGB contains red, green, and blue elements within one package. These LEDs can simulate the appearance of hundreds to thousands of color shades, but cannot produce the actual wavelength of any colors except the constituent of red, green, and blue. For example, the yellow color a viewer sees from an RGB LED does not contain the actual wavelengths of yellow (577 nm to 597 nm). It actually contains the wavelengths of red (about 620 nm) and green (about 525 nm), which when mixed simulate the appearance of yellow.

There is currently no single light source commercially available that can produce a wide range of visible colors, except by mechanically applying various color filters to white light.

It would be highly advantageous, therefore, to remedy the foregoing and other deficiencies inherent in the prior art.

Accordingly, it is an object the present invention to provide a new and improved light/electric probe system and method of use.

Another object of the present invention is to provide a new and improved light/electric probe system with improved light generation and control apparatus.

Another object of the present invention is to provide a new and improved light/electric probe system with improved electric and/or light generation apparatus having improved and highly versatile control apparatus.

SUMMARY OF THE INVENTION

Briefly, to achieve the desired objects of the instant invention in accordance with an embodiment thereof, a stimulation probe system is provided including a hand-held probe with a light source positioned therein. The hand-held probe defines a light output adjacent one end, the light output being positioned to supply light from the light source to a selected point on the surface of a body. Electrical circuitry is coupled to the light source and programmable to regulate the light source, the regulation includes pulse duration and intensity and pulse synchronization.

The desired objects of the instant invention are further achieved in accordance with an embodiment of the invention in which a stimulation probe system includes a light integrating chamber having a light output positioned to supply light from the chamber to the surface of a body. A plurality of light sources is provided with each light source producing a different wavelength of light and the plurality of light sources substantially producing a range of light wavelengths. The plurality of light sources is mounted to introduce emitted light into the chamber. Electrical circuitry is coupled to the plurality of light sources and controllable to produce a variety of light wavelengths and hues. In a preferred embodiment, the plurality of light sources are light emitting diodes. Also, in a preferred embodiment, the light integrating chamber is spherical with a reflecting inner surface and it may be positioned in the hand-held probe or in an external controller with the light communicated to the hand-held probe by some convenient means, such as an optical fiber.

BRIEF DESCRIPTION OF THE DRAWINGS

The foregoing and further and more specific objects and advantages of the invention will become readily apparent to those skilled in the art from the following detailed description taken in conjunction with the drawings in which.

DETAILED DESCRIPTION OF PREFERRED EMBODIMENTS

Figure 1:
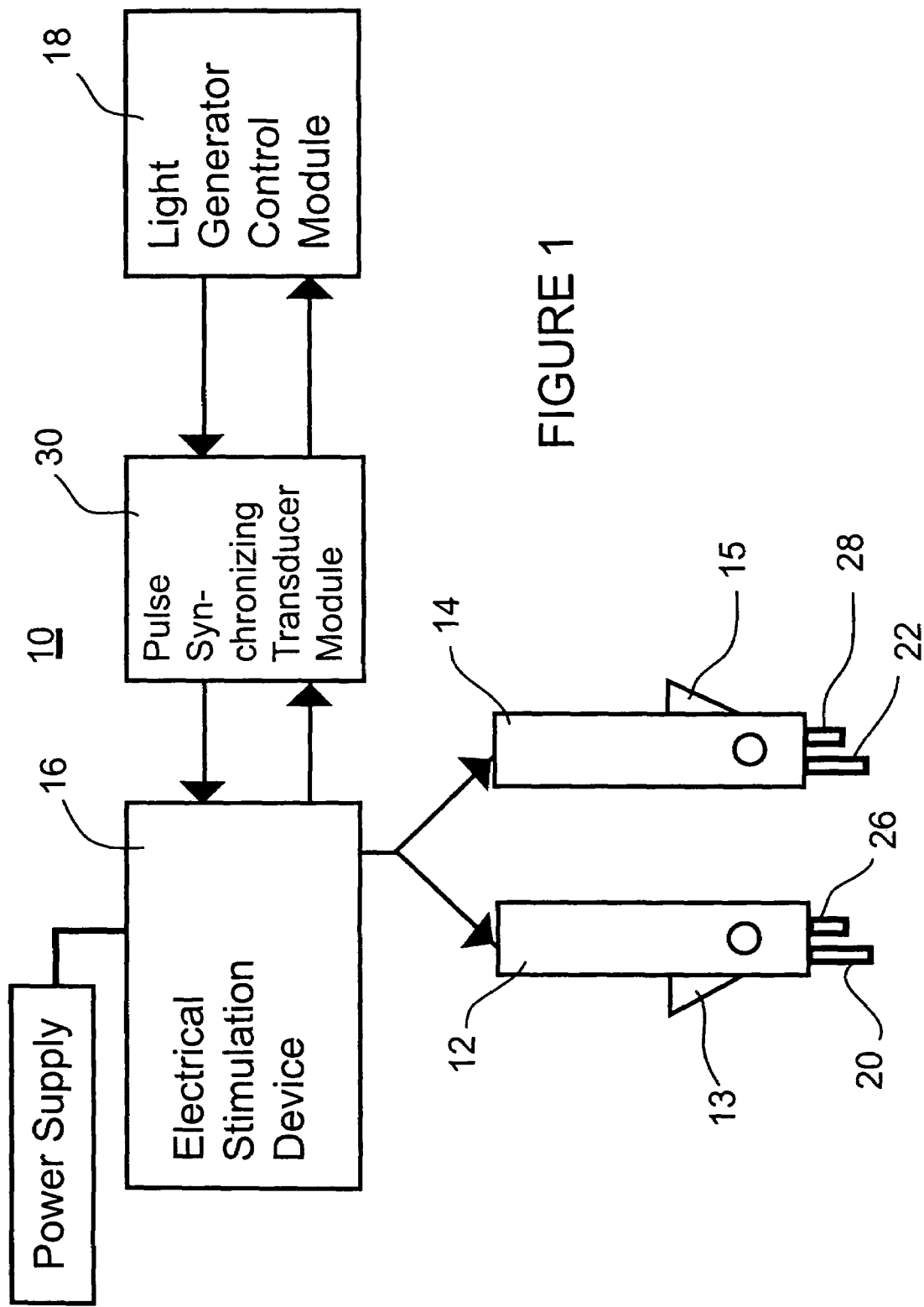
FIG. 1 is a simplified block diagram of a light/electric probe system in accordance with the present invention.

Turning to the drawings, attention is first directed to FIG. 1, which illustrates a light/electric modular probe system 10 in accordance with the present invention. Modular probe system 10 includes one or more hand held probes 12, 14, etc. coupled to a remote controller unit 16. Remote controller unit 16 provides electrical stimulation to electric probe tips 20, 22, etc. at the end of hand held probes 12, 14. Remote controller unit 16 also provides Galvanic Skin Response (GSR) through electrical probe tips 20, 22 to help assess the effects of the stimulation on the body's electrical systems.

Each probe 12, 14 has a trigger switch 13, 15, respectively, to activate current output from that specific probe. Each of the probes 12, 14 include light emitting diode (LED) polarity indicators for the convenience of an operator. The probe handle is isolated from the treatment current so that the treatment current does not affect the operator and vice versa. Also, an electrical stimulation controller within remote controller unit 16 is designed to alter various parameters of the treatment current, e.g. intensity, waveform, frequency, polarity, duration, etc. Since the control of these parameters is well known in the art and in the electrical field generally, a specific description of the control circuit or circuits will not be provided. In this preferred embodiment, electric probe tips 20, 22 are constructed to alternate between measuring GSR or electrical conductivity of the body point, which appears as a read-out at remote controller unit 16, and delivering electrical stimulation to the body point. Again, this alternating read-out and current delivery process is provided by well known logic circuitry and will not be explained in detail herein.

In the preferred embodiment, hand held probes 12, 14 are connected to remote controller unit 16 with light weight, tangle resistant cable of sufficient length for ease of remote use. Triggers 13, 15, as well as the internal light sources, are sealed to prevent the incursion of foreign materials and the consequent degradation in operation. However, hand held probes 12, 14 are constructed to be user serviceable, generally without tools, for general maintenance and cleaning. Also, the modular design allows easy upgrades throughout the life of the system.

A light generator control module 18 may be included in a common chassis with remote controller unit 16 or may be housed separately. Light generator control module 18 regulates light outputs in light delivery tips 26, 28, etc. In this preferred embodiment, light is generated within each probe 12, 14 by means of a light emitting diode (LED), which produces non-coherent light, a semiconductor laser, which produces coherent light, or a combination of the two. As will be explained in detail below, a multi-wavelength light source might be used either in each probe 12, 14 or in module 18 and carried to probes 12, 14 by optical fibers or the like. It is known in the art that coherent and non-coherent light can or may produce different results under certain circumstances. It will of course be understood that other non-coherent light sources could be used but the LED is preferred because of its size and convenience. The generated light is then communicated to the light delivery tips by focusing optics (e.g. small glass or plastic lenses or the like), optical fibers, etc. Light generator control module 18 provides electrical signals to the light sources in hand held probes 12, 14 to regulate the light sources.

Triggers 13, 15 may be designed and connected to actuate the light sources with the application of electric current to electric probe tips 20, 22 in hand held probes 12, 14 or independently. Alternatively, the light sources can be activated remotely in light generator control module 18. Also, light generator control module 18 is designed to alter various parameters of the treatment light provided at light delivery tips 26, 28, e.g. intensity, wavelength—variable across the spectrum, programmable pulse frequency and duration, and customized color blends. Further, light generator control module 18 is designed with preset controls for precision generation of specific colors. So that a user may use preset colors or create customized color blends. Since the control of these parameters is well known in the art and in the optical field generally, a specific description of the control circuit or circuits will not be provided.

Here it will be understood that a variable range of colors, and hues and intensities of each color, can be produced within each hand held probe 12, 14. These variations can be produced by any of a variety of well known methods and apparatus, including but not limited to filters, combinations of light sources, etc. As is known in the art, colors, or hues and intensities of colors, may be inter-mixed to create specific or customized color blends. Further, light delivery tips 26, 28 can include changeable application tips to modify, sharpen, or filter the light output. Light delivery tips 26, 28 may consist of glass lenses, quartz or other minerals or gems, or specialty plastics. Also, light delivery tips 26, 28 can include ultra-violet or infra-red filters.

Each hand held probe 12, 14 may be actuated to provide electrical stimulation only, light stimulation only, or any combination of the two stimulations. Also, a pulse synchronizing module 30 is provided in this embodiment to couple remote controller unit 16 and light generator control module 18 together. Module 30 is capable of synchronizing the light and electrical stimulus if both are used and if synchronization is desired.

Figure 2:
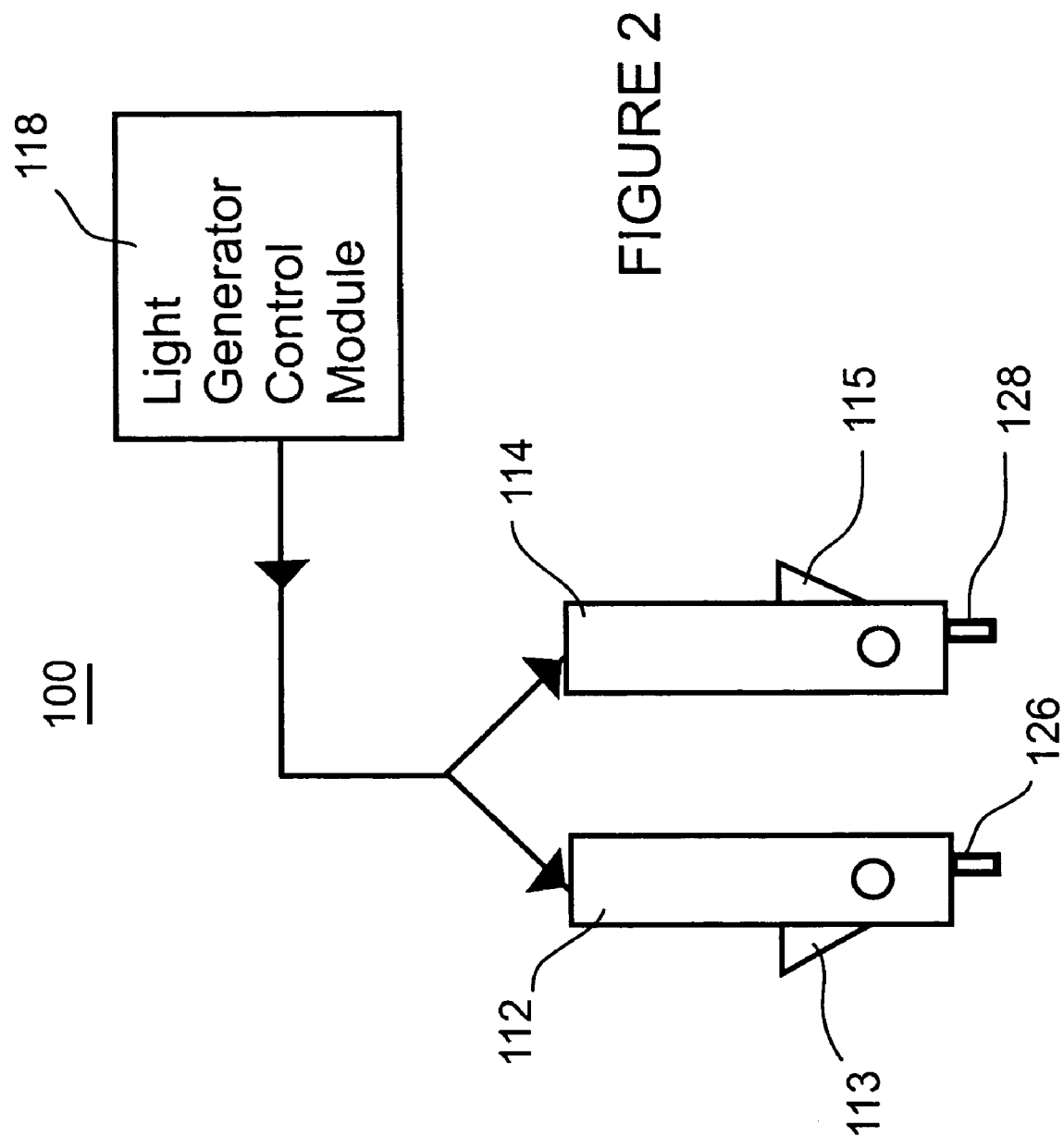
FIG. 2 is an embodiment of a light probe system in accordance with the present invention.

Turning now to FIG. 2, another embodiment is illustrated of a light probe system 100 in accordance with the present invention. In this embodiment light is generated as the only stimulus. Light probe system 100 includes one or more hand held probes 112, 114, etc. coupled to a light generator control module 118. Light generator control module 118 regulates light outputs in light delivery tips 126, 128, etc. In this preferred embodiment, light is generated within each probe 112, 114 by means of a light emitting diode or diodes(LED), which produces non-coherent light, a semiconductor laser, which produces coherent light, or a combination of the two. Generally, light generator control module 118 will operate as described above. The two probes 112, 114 may act independently, that is, each probe may generate different colors or color blends. Alternatively, the two probes 112, 114 may be synchronized to output the same color.

In one specific method of use for the embodiment illustrated in FIG. 1 (i.e. both electrical and light delivery tips), two hand held probes such as 12 and 14 are provided. Each hand held probe includes two treatment tips, one that alternates between measuring GSR and supplying electrical currents, and one that emits light. The two tips of each probe target the same point on the body, thus applying simultaneous electric and light stimulation to that point, or set of points. In this specific method, remote controller unit 16 defines the electrical polarities of the two probes 12 and 14. That is, when one probe (e.g. probe 12) is negatively polarized probe 14 is positively polarized and vice versa. The LED indicator glows on the probe delivering a reference polarity. For example, the default setting is for the negatively polarized probe LED to glow, although this can be changed by user preference.

Figure 3:
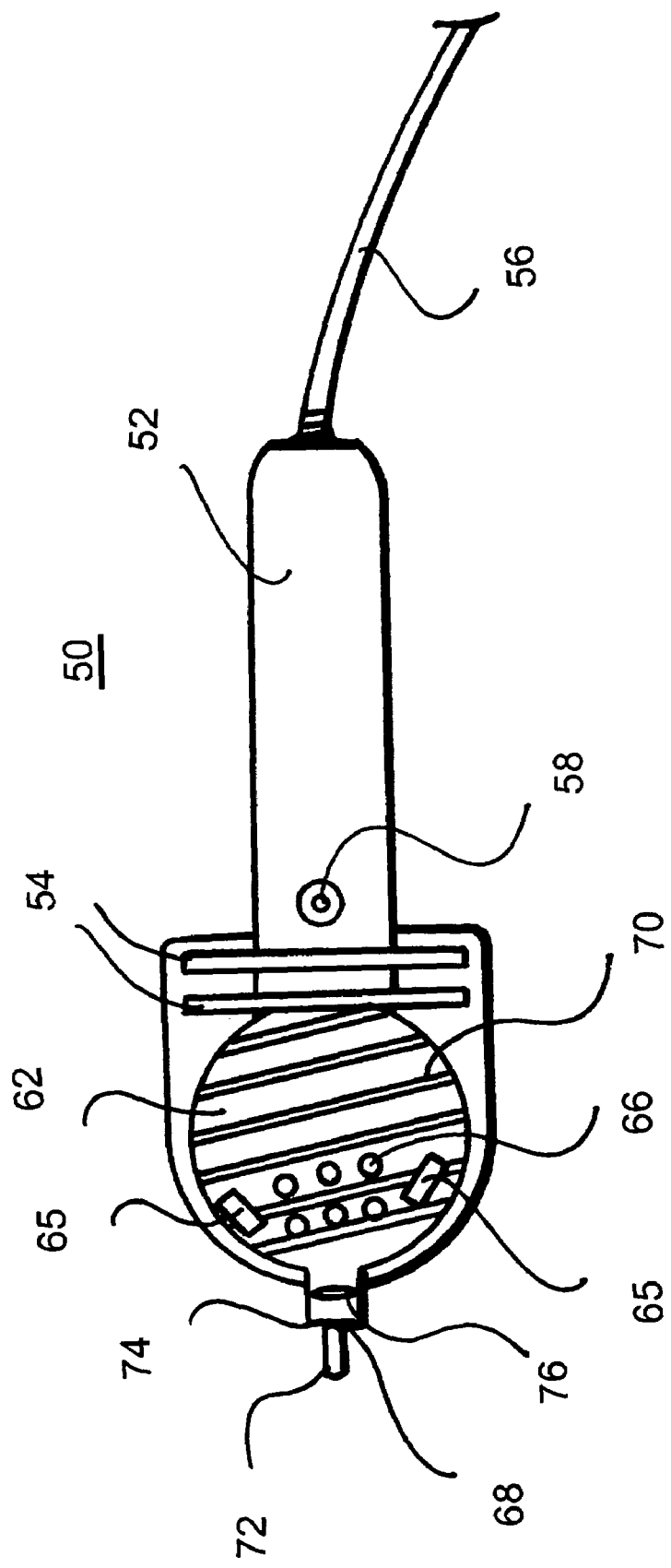
FIG. 3 is a simplified side view, portions thereof removed to show internal components, of another embodiment of a light/electric probe system in accordance with the present invention.
Figure 4:
FIG. 4 is a front view of a remote controller for the light/electric probe system of FIG. 3, in accordance with the present invention.

Turning now to FIG. 3, another embodiment is illustrated of a light/electric probe system, generally designated 50, in accordance with the present invention. Light/electric probe system 50 includes a handle 52 with one or more electrical circuit boards 54 mounted thereon in some convenient position. A power cord 56 is connected to electrical circuit boards 54 to supply appropriate power or other control signals thereto. Power cord 56 extends from electrical circuit boards 54, through handle 52, and to an appropriate control signal and/or power source, such as a remote control unit 60, illustrated in FIG. 4 and discussed in more detail below. In this specific embodiment an on-off switch 58 is supplied on handle 52 for the control of power to electrical circuit boards 54.

A light integrating spherical light chamber 62 is positioned at the end of handle 52 opposite power cord 56. Chamber 62 can be mounted on one of electrical circuit boards 54, for convenience in providing internal electrical connections. In this preferred embodiment a plurality of LEDs 65, generally producing a range of colors, are mounted around the outer circumference of chamber 62 so as to emit light into chamber 62 through small openings 66 in chamber 62. Here it will be understood that LEDs 65 will substantially produce a range of colors, i.e. some gaps in the range may occur because of an inability to provide certain colors in LEDs. LEDs 65 are electrically connected to at least one of electrical circuit boards 54 by leads extending along the outer surface of chamber 62. LEDs 65 and openings 66 are positioned so that light emitted from the LEDs is directed diagonally toward the base of the sphere at what results in various angles. Also LEDs 65 are chosen so that each LED emits a different color (wavelength) of light. In this preferred embodiment, the inner surface of chamber 62 is white and reflective so that colors from the various LEDs are mixed or integrated. Also, a light exit opening 68 is provided at a position in chamber 62 substantially opposite to the axial direction of handle 52. While a specific integrating chamber and light source (LEDs 65) are disclosed herein because of their ease of manufacturing, it will be understood that other light sources and other devices for integrating colors may be utilized in specific applications.

A wire coil 70 is formed on the outer surface of spherical chamber 62 with one end electrically coupled to at least one of electrical circuit boards 54 for receiving appropriate electrical signals. In this preferred embodiment an electric probe tip 72 is axially mounted in the center of light exit opening 68 so as to extend outwardly beyond the edges of light exit opening 68. Probe tip 72 is electrically coupled to coil 70, either through direct connection or through inductance, to receive electrical stimulation signals from at least one of electrical circuit boards 54.

In this preferred embodiment, probe tip 72 is mounted substantially in the center of light exit opening 68 by means of a tripod-like holder 74 formed with very thin fins that extend radially between probe tip 72 and the inner periphery of light exit opening 68. Holder 74 is designed to minimize blockage of light emanating from chamber 62 through light exit opening 68. Also, in this preferred embodiment, a focusing lens 76 is mounted in light exit opening 68 to focus the light output of probe system 50 to a desired diameter spot on a target surface, i.e. at approximately the outer extent of probe tip 72. For example, during use the extreme end of probe tip 72 is applied to the surface of a human or animal body and, the light output from light exit opening 68 is focused on the surface of the body surrounding the extreme end of probe tip 72.

As explained above in conjunction with FIGS. 1 and 2, in some applications it may be desirable to provide a probe with only a variable light stimulation output. In such instances, probe system 50 may be provided with only the light stimulation portion and without the electrical stimulation portion (i.e. wire coil 70 and probe tip 72). Further, as explained in conjunction with FIGS. 1 and 2 above, two or more probes 50 with electrical and/or light stimulation can be used simultaneously. Also, in the preferred embodiment in which electrical stimulation is included, electrical probe tip 72 is alternated by an internal microprocessor between measuring the GSR, or electrical conductivity of the contact point, and delivering electrical stimulation.

In the preferred embodiment, a microprocessor, digital signal processor, or similar programmable device is mounted on one of the electrical circuit boards 54, along with any circuits required to perform the desired functions. Through the use of remote control unit 60, for example, in conjunction with programs stored in the microprocessor precise selection of color wavelengths of light, adjustment of hue and intensity of color, and customized blends of colors of light, with or without simultaneous electrical stimulation, can be achieved. For example, power cord 56 of probe system 50, in this embodiment, is constructed with a signal bus designed to carry various electrical signals between the microprocessor and associated circuitry and remote control unit 60. The microprocessor is programmed to send a series of queries to remote control unit 60, for example, "select a color wavelength of light", "select an intensity of light", etc. As each of the queries appears in the display of remote control unit 60, the operator inputs the numbers desired by using the keyboard. The microprocessor is programmed to automatically actuate the LEDs 65 which will provide the specified wavelength or wavelengths, the intensity, etc. The microprocessor may be programmed, through remote control unit 60, to output a sequence of colors, with colors and on times selected by the user. Also, the light and/or electrical stimulation output can be set by remote control unit 60 to one of the following modes: continuous light, flashing at the same rate as the electrical frequency, out-of-phase flashing, synchronization with external sound source, and discrete flash rate from 1–10 Hz. Once the procedure is completed, the 'enter' key may be pressed to begin the therapy.

Because a plurality of different LEDs 65 are provided with chamber 62, a large variety of color wavelengths, hues, customized blends, and intensities (possibly by providing more than one LED of each variety) can be achieved simply by activating one or more of the same and/or different LEDs simultaneously. Because of the geometry of the sphere (chamber 62), the various colors emitted reflect within the sphere numerous times, producing an effective blending of the various colors. Further, because of the variety of different LEDs, a wide range of the actual wavelengths of colored light is produced, well beyond what is possible in prior art devices.

In addition, any external digital sound source, such as but not limited to, a CD player playing music, a tone generator creating tones, etc. may be supplied to the microprocessor through remote control unit 60, additionally or alternatively, remote control unit 60 may include a microprocessor. Through programming of one or both of the microprocessors, the light and/or electrical stimulation can be synchronized to the digital sound source. For example, the pulse rate and color selection of the light emission can be synchronized with a sound input for a harmonized output. When more than one probe system 50 is used simultaneously, the probes may be programmed to operate together or in different relationships with each other, e.g. independent, parallel, in/out of phase, etc.

Thus, a light/electric probe system and method is disclosed that includes the following advantages and purposes. A method for generation of white or colored light within a treatment probe, or set of probes, or other devices, that allows for precise selection of color wavelengths of light, and adjustment of hue and intensity of color, and customized blends of colors of light, with or without simultaneous electrical stimulation. The application of simultaneous electrical and light stimulation through one or more treatment probes to regions and specific points on the surface of the human and animal bodies for beneficial health and beauty effects. The apparatus allows precise calibration of electrical parameters such as intensity, frequency, waveform, polarity, and modulation for probe stimulation as well as precise calibration of light parameters such as hue, wavelength (color), intensity, and in or out-of-phase relationship of the output of multiple probes. By adjusting both electrical and light parameters with precision, positive resonance with bodily tissues and energy systems can be achieved in a greater percentage of cases. The apparatus further allows for the frequency of electrical stimulation and the wavelengths of light stimulation to be synchronized with each other, in various relationships, for maximum benefit. Also, the apparatus allows for measurement of GSR through the electrical probe tip to help assess the effects of the stimulation on the body's electrical systems.

The invention has been described above with reference to one or more preferred embodiments. However, those skilled in the art will recognize that changes and modifications may be made in the described embodiments without departing from the nature and scope of the invention. For example, light sources other than LEDs might be utilized in conjunction with a different form of integrating chamber. Also, the integrating chamber and light sources might be positioned in the remote control unit and the resulting light carried to the tip by optical fibers or other light conducting means. In this instance the microprocessor and other controls would by contained in the remote control unit. To illustrate this structure, the integrating chamber could be positioned in light generator control model 18 of FIG. 1 and the light carried to tips 26 and 28 by optical fibers.

Various changes and modifications to the embodiments herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same, the invention claimed is:

1. A stimulation probe system comprising:
a light integrating chamber having a light output positioned to supply light from the chamber to the surface of a body;
a plurality of light sources, each light source producing a different wavelength of light and the plurality of light sources substantially producing a range of light wavelengths, the plurality of light sources mounted to introduce emitted light into the chamber, wherein the light integrating chamber and plurality of light sources are located in a hand-held probe; and
electrical circuitry coupled to the plurality of light sources and controllable to produce a variety of light wavelengths and hues.

2. A stimulation probe system as claimed in claim 1 wherein the light integrating chamber includes a spherical chamber with a reflecting inner surface and openings in the surface for receiving light from the plurality of light sources.

3. A stimulation probe system as claimed in claim 1 wherein the plurality of light sources includes a plurality of light emitting diodes, each light emitting diode producing a different wavelength of light when activated.

4. A stimulation probe system as claimed in claim 1 wherein the electrical circuitry includes a microprocessor coupled to the plurality of light sources and programmable to activate at least one of the plurality of light sources to produce substantially any light wavelength available from the plurality of light sources.

5. A stimulation probe system as claimed in claim 1 further including an electrical stimulation tip mounted in the hand-held probe and coupled to a source of electrical stimulation.

6. A stimulation probe system as claimed in claim 5 wherein the light output of the light integrating chamber includes a circular opening at an end of the hand-held probe and the electrical stimulation tip is positioned substantially coaxially within the circular opening.

7. A stimulation probe system as claimed in claim 6 wherein the light output of the light integrating chamber includes a focusing lens positioned adjacent the circular opening and focuses the light output at an extremity of the electrical stimulation tip.

8. A stimulation probe system comprising:
   a light integrating chamber having a light output positioned to supply light from the chamber to the surface of a body;
   a plurality of light sources, each light source producing a different wavelength of light and the plurality of light sources substantially producing a range of light wavelengths, the plurality of light sources mounted to introduce emitted light into the chamber; and
   electrical circuitry coupled to the plurality of light sources and controllable to produce a variety of light wavelengths and hues, wherein the electrical circuitry includes a processor coupled to the plurality of light sources and having an external electrical signal input for synchronizing light produced by the plurality of light sources with an external signal supplied to the external electrical signal input.

9. A stimulation probe system comprising:
   a light integrating chamber with a reflecting inner surface and a light output;
   a hand-held probe including a circular opening at an end thereof in optical communication with the light output of the light integrating chamber and positioned to supply light from the chamber to the surface of a body;
   a plurality of light emitting diodes, each light emitting diode producing a different wavelength of light and the plurality of light emitting diodes substantially producing a range of light wavelengths, the plurality of light emitting diodes mounted to introduce emitted light into the light integrating chamber;
   electrical circuitry including a microprocessor coupled to the plurality of light emitting diodes, the microprocessor being programmable to activate at least one of the plurality of light emitting diodes to produce substantially any light wavelength available from the plurality of light emitting diodes and controllable to produce a variety of light wavelengths and hues; and
   an electrical stimulation tip mounted in the hand-held probe, substantially coaxially within the circular opening, and coupled to a source of electrical stimulation, the electrical stimulation tip including an extremity designed to contact the surface of the body.

10. A stimulation probe system as claimed in claim 9 wherein the light output of the light integrating chamber includes a focusing lens positioned adjacent the circular opening, the lens focusing the light output at the extremity of the electrical stimulation tip.

11. A stimulation probe system as claimed in claim 9 wherein the light integrating chamber includes a substantially spherical chamber including a white, reflecting inner surface.

12. A stimulation probe system comprising:
   a hand-held probe including a light source positioned therein with a light output adjacent one end of the probe, the light output being positioned to supply light from the light source to a selected point on the surface of a body;
   the light source positioned in the hand-held probe includes a spherical light integrating chamber with a reflecting inner surface and a plurality of light emitting diodes, each light emitting diode producing a different wavelength of light and the plurality of light emitting diodes substantially producing a range of light wavelengths, the plurality of light emitting diodes being mounted to introduce emitted light into the spherical light integrating chamber; and
   electrical circuitry coupled to the light source and programmable to regulate the light source, the regulation including pulse duration and intensity and pulse synchronization, the electrical circuitry includes a microprocessor coupled to the plurality of light emitting diodes.

13. A stimulation probe system as claimed in claim 12 wherein the microprocessor is programmable to activate at least one of the plurality of light emitting diodes to produce substantially any light wavelength available from the plurality of light emitting diodes and controllable to produce a variety of light wavelengths and hues.

14. A stimulation probe system comprising:
   a hand-held probe including a light source positioned therein with a light output adjacent one end of the probe, the light output being positioned to supply light from the light source to a selected point on the surface of a body;
   electrical circuitry coupled to the light source and programmable to regulate the light source, the regulation including pulse duration and intensity and pulse synchronization; and
   an electrical stimulation tip coupled to the electrical circuitry and mounted in the hand-held probe, substantially coaxially within the light output of the light source.

15. A method of stimulating portions of a body comprising the steps of:
   providing a stimulation probe system including a light integrating chamber with a light output, a hand-held probe including a circular opening at an end thereof in optical communication with the light output of the light integrating chamber, a plurality of light emitting diodes each producing a different wavelength of light in a range of light wavelengths and mounted to introduce emitted light into the light integrating chamber; and
   electrical circuitry coupled to the plurality of light emitting diodes and programmable to activate at least one of the plurality of light emitting diodes to produce substantially any light wavelength available from the plurality of light emitting diodes and controllable to produce a variety of light wavelengths and hues;
   programming the electrical circuitry to produce pulses of a selected wavelength of light; and
   activating the probe system and positioning the circular opening of the hand held probe adjacent a surface of a body with the pulses of the selected wavelength of light impinging on the surface of the body.

16. A method as claimed in claim 15 wherein the step of providing a stimulation probe system includes providing two substantially identical hand held probes and the step of positioning includes positioning both hand-held probes simultaneously at different points on the surface of the body.

17. A method as claimed in claim 15 wherein the step of providing a stimulation probe system includes providing an electrical stimulation tip coupled to the electrical circuitry and mounted in the hand-held probe, substantially coaxially within the light output of the light source and the programming step includes programming the electrical circuitry to produce pulses of a selected electrical stimulation.

18. A method as claimed in claim 17 wherein the step of positioning the circular opening of the hand held probe adjacent a surface of a body includes touching an extremity of the electrical stimulation tip to the surface of the body.

19. A method as claimed in claim 18 wherein the step of programming the electrical circuitry includes introducing external sound signals and synchronizing at least one of the pulses of the selected wavelength of light and the pulses of the selected electrical stimulation with the external sound signals.

20. A method as claimed in claim 19 wherein the step of providing a stimulation probe system includes providing two substantially identical hand held probes and the step of positioning includes positioning both hand-held probes simultaneously at different points on the surface of the body.

* * * * *